US008889164B2

(12) United States Patent
Hashimoto et al.

(10) Patent No.: US 8,889,164 B2
(45) Date of Patent: Nov. 18, 2014

(54) ANTIMICROBIAL AND ANTIVIRAL COMPOSITION, AND METHOD OF PRODUCING THE SAME

(71) Applicants: Kazuhito Hashimoto, Bunkyo-ku (JP); Kayano Sunada, Bunkyo-ku (JP); Masahiro Miyauchi, Bunkyo-ku (JP); Ding Li, Toyama (JP); Yasushi Kuroda, Toyama (JP)

(72) Inventors: Kazuhito Hashimoto, Bunkyo-ku (JP); Kayano Sunada, Bunkyo-ku (JP); Masahiro Miyauchi, Bunkyo-ku (JP); Ding Li, Toyama (JP); Yasushi Kuroda, Toyama (JP)

(73) Assignees: Showa Denko K.K., Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 13/878,026

(22) PCT Filed: Oct. 4, 2012

(86) PCT No.: PCT/JP2012/076375
§ 371 (c)(1),
(2), (4) Date: Apr. 5, 2013

(87) PCT Pub. No.: WO2013/054860
PCT Pub. Date: Apr. 18, 2013

(65) Prior Publication Data
US 2014/0199357 A1    Jul. 17, 2014

(30) Foreign Application Priority Data
Oct. 12, 2011   (JP) ................. 2011-224529

(51) Int. Cl.
*A01N 59/20* (2006.01)
*A01N 25/00* (2006.01)
(52) U.S. Cl.
CPC ..................... *A01N 59/20* (2013.01)
USPC ........................... 424/405; 424/635
(58) Field of Classification Search
None
See application file for complete search history.

(56) References Cited

U.S. PATENT DOCUMENTS

2013/0344124 A1* 12/2013 Hashimoto et al. ........... 424/419

FOREIGN PATENT DOCUMENTS

| CN | 101322939 A | 12/2008 |
|---|---|---|
| JP | 2003-528975 A | 9/2003 |
| JP | 2006-506105 A | 2/2006 |
| JP | 2007-504291 A | 3/2007 |
| JP | 2008-518712 A | 6/2008 |
| JP | 2009-526828 A | 7/2009 |
| JP | 4401197 B2 | 11/2009 |
| JP | 4401198 B2 | 1/2010 |
| JP | 4473607 B2 | 6/2010 |
| JP | 2010-168578 A | 8/2010 |
| JP | 4646210 B2 | 3/2011 |
| JP | 2011-1153163 A | 8/2011 |
| WO | 2007/093808 A2 | 8/2007 |
| WO | 2011/078203 A1 | 6/2011 |

OTHER PUBLICATIONS

International Search Report and Written Opinion issued in PCT/JP2012/076375 dated Jan. 2, 2013.

* cited by examiner

*Primary Examiner* — Tracy Vivlemore
*Assistant Examiner* — Monica Shin
(74) *Attorney, Agent, or Firm* — Sughrue Mion, PLLC

(57) ABSTRACT

An antimicrobial and antiviral composition, a method of producing the same, and the like are provided, which are capable of exhibiting an excellent antimicrobial and antiviral properties over a long time in the application for various uses. The antimicrobial and antiviral composition contains cuprous oxide particles having a BET specific surface area of 5 to 100 $m^2/g$ and a saccharide having an aldehyde group, in which the content of the saccharide with an aldehyde group is 0.5 to 10 mass part based on the cuprous oxide particles of 100 mass part. The method produces this composition.

11 Claims, 2 Drawing Sheets

(A) Example 1

(A) Example 1

(B) Comparative Example 1

ANTIMICROBIAL AND ANTIVIRAL COMPOSITION, AND METHOD OF PRODUCING THE SAME

CROSS REFERENCE TO RELATED APPLICATIONS

This application is a National Stage of International Application No. PCT/JP2012/076375 filed Oct. 4, 2012, claiming priority based on Japanese Patent Application No. 2011-224529, filed Oct. 12, 2011, the contents of all of which are incorporated herein by reference in their entirety.

TECHNICAL FIELD

The present invention relates to an antimicrobial and antiviral composition and a method of producing the same, and a dispersion of the antimicrobial and antiviral composition, a coating agent containing the antimicrobial and antiviral composition, an antimicrobial and antiviral film, and an antimicrobial and antiviral article which are applied to construction materials, sanitary materials, antifouling materials, and the like in a living environment.

BACKGROUND ART

The copper (II) ion is known as an effective ingredient for antimicrobial and antiviral properties. For example, patent document 1 discloses an antimicrobial and antiviral polymeric material having microscopic particles of ionic copper encapsulated therein and protruding form surfaces there of.

Patent documents 2-4 disclose that a copper (I) compound has antimicrobial and antiviral performance superior to a copper (II) compound.

Patent document 5 discloses that nanoparticles consisting of a mixed composition of copper, copper (II) oxide, and cuprous oxide have excellent antimicrobial and antiviral performance.

It is reported that a saccharide having a reducing aldehyde group, as typified by glucose or the like, is used as a reducing agent for the synthesis of cuprous oxide. For example, patent documents 6-8 disclose that reducing sugar, such as glucose, is used for the synthesis of several-micrometers of cuprous oxide with various shapes.

In addition, the study is known, in which a copper compound is supported on a photocatalytic material to provide antimicrobial and antiviral performance. For example, patent document 9 discloses a deactivator for phage viruses, which consists of copper (II) oxide-supported titanium oxide, for deactivating viruses under ultraviolet irradiation.

Patent document 10 discloses that copper (I) oxide-supported titanium oxide demonstrates antiviral performance. Patent document 11 discloses that copper (I) oxide demonstrates high antimicrobial and antiviral performance.

CITATION LIST

Patent Literature

Patent document 1: JP2003-528975 A
Patent document 2: JP2006-506105 A
Patent document 3: JP2007-504291 A
Patent document 4: JP2008-518712 A
Patent document 5: JP2009-526828 A
Patent document 6: JP4401197 C
Patent document 7: JP4401198 C
Patent document 8: JP4473607 C
Patent document 9: JP4646210 C
Patent document 10: CN101322939 A
Patent document 11: JP2011-153163 A

SUMMARY OF INVENTION

Technical Problem

As a copper (I) compound that demonstrates excellent antimicrobial and antiviral properties, cuprous oxide is known. In fact, pure cuprous oxide nanoparticles are unstable in the air to be oxidized into copper (II) oxide ones gradually, causing the antimicrobial and antiviral performance to be lowered. However, patent documents 1-4 do not disclose such a problem with lowering antimicrobial and antiviral properties.

Patent document 5 does not disclose that cuprous oxide nanoparticles are evaluated alone or that there is the problem in which cuprous oxide nanoparticles are oxidized easily in the air, causing the antimicrobial and antiviral properties to be lowered.

In patent documents 6-8, a reducing agent is removed after cuprous oxide is synthesized. The cuprous oxide powder obtained by any of the methods described in these literatures is oxidized easily in the atmosphere, so that the antimicrobial and antiviral properties may be lowered. Furthermore, micrometer-sized cuprous oxide obtained by any of the methods described in these literatures has a smaller specific surface area, so that the antimicrobial and antiviral performance may be lowered.

Patent document 9 does not disclose that cuprous oxide demonstrates extremely high antimicrobial and antiviral performance. For the use of antimicrobial and antiviral application, cuprous oxide has a greater antimicrobial and antiviral effect than copper (II) oxide when these oxides are maintained on the surface of titanium oxide. Furthermore, patent document 9 does not describe the advantage that copper (II) oxide, into which cuprous oxide nanoparticles are oxidized in the air, is reduced into cuprous oxide with a photocatalyst to sustain the antimicrobial and antiviral effect.

The cuprous (I) oxide-supported titanium oxide described in patent document 10 does not differ from those described any of the above-mentioned literatures in that it is easily oxidized in the atmosphere, so that the antimicrobial and antiviral properties may be lowered.

Even in patent document 11, the cuprous oxide (I) is easily oxidized in the air, so that the antimicrobial and antiviral performance may be lowered. On this point, patent document 11 does not disclose a method of inhibiting the oxidation of cuprous oxide (I).

An object of the present invention is to provide an antimicrobial and antiviral composition, a method of producing the same, and a dispersion of the antimicrobial and antiviral composition, which are capable of exhibiting an excellent antimicrobial and antiviral effect over a long time in the application for various uses. Another object of the present invention is to provide a coating agent containing the antimicrobial and antiviral composition, an antimicrobial and antiviral film, and an antimicrobial and antiviral article, which are capable of exhibiting an excellent antimicrobial and antiviral effect over a long time.

Solution to Problem

The inventors have found that it is important to have cuprous oxide particles and a saccharide having a reducing aldehyde group (hereafter sometimes referred to as "reducing sugar") coexist in a specific amount so that cuprous oxide particles exhibiting an excellent antimicrobial and antiviral properties are stably maintained without being oxidized into copper (II) oxide ones in the air. In other word, the inventors have found that the existence of reducing sugar in a specific amount maintains the excellent antimicrobial and antiviral properties of cuprous oxide for a long time. Furthermore, the inventors have found that the combination with a photocatalytic material reduces copper (II) oxide, which have lost the antimicrobial and antiviral properties due to oxidization, into cuprous oxide ones by light irradiation, so that the effect can be sustained almost permanently. Yet furthermore, the inventors have found that a specific visible light responsive photocatalyst is used as the photocatalytic material, so that the antimicrobial and antiviral properties can be sustained almost permanently under visible light irradiation.

Specifically, the present invention is as follows aspects:

(1) An antimicrobial and antiviral composition, comprising cuprous oxide particles having a BET specific surface area of 5 to 100 $m^2/g$; and a saccharide having an aldehyde group, wherein the content of the saccharide having an aldehyde group is 0.5 to 10 mass part based on the cuprous oxide particles of 100 mass part.

(2) The antimicrobial and antiviral composition as described in the above aspect (1), further comprising a photocatalytic material, wherein the content of the photocatalytic material is 70 to 99.9% by mass based on the total amount of the cuprous oxide particles, the saccharide having an aldehyde group, and the photocatalytic material.

(3) The antimicrobial and antiviral composition as described in the above aspect (2), wherein the photocatalytic material comprises at least one selected from titanium oxide and tungsten oxide.

(4) The antimicrobial and antiviral composition as described in the above aspect (2) or (3), wherein the photocatalytic material is a visible light responsive photocatalyst in which a substrate selected from (A) titanium oxide and tungsten oxide is modified with at least one selected from (B) a copper (II) ion and an iron (III) ion.

(5) The antimicrobial and antiviral composition as described in the above aspect (2) or (3), wherein the photocatalytic material is a visible light responsive photocatalyst in which a substrate selected from the group consisting of (C) titanium oxide doped with a transition metal; titanium oxide doped with at least one non-metal of carbon, nitrogen, and sulfur; tungsten oxide doped with a transition metal; and tungsten oxide doped with at least one non-metal of carbon, nitrogen, and sulfur is modified with at least one selected from (B) a copper (II) ion and an iron (III) ion.

(6) A dispersion of the antimicrobial and antiviral composition, comprising 1 to 30% by mass of the antimicrobial and antiviral composition as described in any one of the above aspects (1) to (5); 60 to 98.99% by mass of a non-aqueous organic solvent; and 0.01 to 10% by mass of a basic substance being soluble in the non-aqueous organic solvent.

(7) A dispersion of the antimicrobial and antiviral composition, comprising 1 to 30% by mass of the antimicrobial and antiviral composition as described in any one of the above aspects (1) to (5), 40 to 98.99% by mass of a non-aqueous organic solvent, 0.01 to 10% by mass of a basic substance being soluble in the non-aqueous organic solvent, and 0.01 to 20% by mass of a surfactant being soluble in the non-aqueous organic solvent.

(8) A coating agent containing the antimicrobial and antiviral composition, comprising the dispersion of the antimicrobial and antiviral composition as described in the above aspect (6) or (7), a binder component being curable under an environment of 10-120° C.

(9) An antimicrobial and antiviral film which the coating agent containing the antimicrobial and antiviral composition as described in the above aspect (8) is applied and then cured.

(10) An antimicrobial and antiviral article comprising the antimicrobial and antiviral film as described in the above aspect (9) on at least one part of the surface.

(11) A method of producing an antimicrobial and antiviral composition, comprising the steps of: adding a basic substance and a reducing agent other than a saccharide having an aldehyde group in aqueous solution of a copper (II) compound and then synthesizing cuprous oxide particles; mixing the obtained cuprous oxide particles with aqueous solution of a saccharide having an aldehyde group to adjust the content of a saccharide having an aldehyde group to from 0.5 to 10 mass part based on the obtained cuprous oxide particles of 100 mass part; and separating a solid content from the mixture and then pulverizing the solid content.

Advantageous Effects of Invention

The present invention can provide an antimicrobial and antiviral composition, a method of producing the same, and a dispersion of the antimicrobial and antiviral composition, which are capable of exhibiting an excellent antimicrobial and antiviral effect over a long time in the application for various uses. The present invention can also provide a coating agent containing the antimicrobial and antiviral composition, an antimicrobial and antiviral film, and an antimicrobial and antiviral article that are capable of exhibiting an excellent antimicrobial and antiviral effect over a long time.

For example, it can be expected that applying a coating agent containing the antimicrobial and antiviral composition of the present invention to an article or a part thereof to be touched by an unspecified number of people decreases the risk for the spread of microbes and viruses from one person to another through the surface of this article.

DESCRIPTION OF EMBODIMENTS

Figure 1:
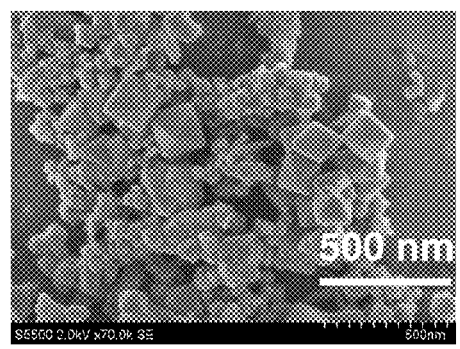
FIG. 1 shows a SEM image of the cuprous oxide particles obtained in Example 1.

Antimicrobial and Antiviral Composition and Method of Producing the Same

The antimicrobial and antiviral composition of the present invention contains cuprous oxide particles having a BET specific surface area of 5 to 100 $m^2/g$ and a saccharide with an aldehyde group. While the cuprous oxide particles having a BET specific surface area of 5 to 100 $m^2/g$ has high antimicrobial and antiviral properties, it is difficult to exhibit an excellent antimicrobial and antiviral effect over a long time due to the high oxidability. In the present invention, a saccharide having an aldehyde group is allowed to coexist to maintain the excellent antimicrobial and antiviral properties of cuprous oxide particles. However, if a saccharide having an aldehyde group is contained too little, the oxidability of cuprous oxide particles cannot be suppressed. If a saccharide having an aldehyde group is contained too much, the antimicrobial and antiviral properties of cuprous oxide particles are inhibited. In the present invention, the content of the saccharide with an aldehyde group is adjusted to 0.5 to 10% by mass based on the cuprous oxide particles of 100 mass part to suppress the oxidability of cuprous oxide particles and to achieve the excellent antimicrobial and antiviral properties.

Cuprous Oxide Particles

The cuprous oxide particles used in the present invention are represented by the chemical formula of $Cu_2O$. The shape of the cuprous oxide particles observed with an electron microscope is not particularly limited. However, the cuprous oxide particles are octahedral crystals, and indeterminate almost-spherical shape. In the present invention, any one of these shape may exist alone or may be mixed in any combination.

The cuprous oxide particles according to the present invention has a BET specific surface area of 5 to 100 $m^2/g$, preferably 10 to 50 $m^2/g$, more preferably 20 to 40 $m^2/g$, calculated by a nitrogen adsorption method (BET method). The cuprous oxide particles having a BET specific surface area of 5-100 $m^2/g$ can exhibit high antimicrobial and antiviral properties. However, the cuprous oxide particles having a BET specific surface area of more than 100 $m^2/g$ are hardly synthesized or collected, and then hardly handled. On the other hand, the cuprous oxide particles with a BET specific surface area of less than 5 $m^2/g$ have a few contact points with microbes or viruses, showing a small antimicrobial and antiviral effect. In this case, the obtained cuprous oxide particles become dark orange brown. If these particles are used for an antimicrobial and antiviral coating agent, the problem arises, in which the design of an article coated with this agent is impaired.

The smaller the particle diameter of cuprous oxide is, the higher antimicrobial and antiviral performance is. In addition, it is known that cuprous oxide becomes transparent by the quantum size effect when pulverized finely. In this case, the antimicrobial and antiviral performance is also increased, so that the amount used can be decreased, leading to the reduced coloration. Thus, the cuprous oxide as an antimicrobial and antiviral material is preferable in a smaller microparticle form. However, as the particle diameter is smaller, the cuprous oxide particles are more easily oxidized into copper (II) oxide ones in the air. It is known that copper (II) oxide is black, causing the design of an article coated with copper (II) oxide to be impaired and degrading the antimicrobial and antiviral performance.

Therefore, for the particle diameter of cuprous oxide particles, the primary particle diameter determined from the maximum particle diameter confirmed with an electron microscope falls within the range of preferably 1 to 400 nm, more preferably 5 to 150 nm, further more preferably 10 to 50 nm.

Saccharide having Aldehyde Group

The saccharide having an aldehyde group (—CHO) used in the present invention is preferably at least one selected from the group of saccharides which are commonly referred to as "aldose", and may be a monosaccharide, a polysaccharide, or a mixture thereof. As an example, the saccharide includes glucose, xylose, galactose, fructose, maltose, and lactose. Among these, in consideration of ready availability, prices, and the like, glucose, xylose, and galactose are more preferable, and glucose is the most preferable.

The content of the saccharide having an aldehyde group is 0.5 to 10 mass part based on the cuprous oxide particles of 100 mass part. If the content is smaller than 0.5 mass part, the antioxidant effect is insufficient. On the other hand, if the content is larger than 10 mass part, the antimicrobial and antiviral performance is decreased. The content is preferably 1.0 to 7 mass part, more preferably 1.0 to 5 mass part, further more preferably 1.0 to 3.0 mass part, the most preferably 1.3 to 2.0 mass part.

The content of the saccharide having an aldehyde group means the total amount of saccharides including isomers such as a chain isomer and a cyclic isomer.

Photocatalytic Material

The antimicrobial and antiviral composition of the present invention may contain a photocatalytic material. The content of the photocatalytic material in the total amount (of the antimicrobial and antiviral composition including a photocatalytic material) is preferably 70 to 99.9% by mass. Containing a photocatalytic material can reduce copper (II) oxide, which has been changed from copper oxide (I) and then have lost the antimicrobial and antiviral properties, into cuprous oxide by light irradiation. As a result, the antimicrobial and antiviral performance can be sustained almost permanently.

The content of the photocatalytic material in the total amount (of the antimicrobial and antiviral composition including a photocatalytic material) is more preferably 80 to 99% by mass, further more preferably 90 to 98% by mass.

The photocatalytic material is not particularly limited as long as it has redox ability under light irradiation. The photocatalytic material includes compound semiconductors, such as metal oxide and metal oxynitride. From the viewpoint of versatility, the photocatalytic material includes titanium oxide or tungsten oxide as a main component, preferably titanium oxide as a main component. The "main component" means a component contained in 60% by mass or more in a photocatalytic material.

Titanium oxide is known to have crystal structures of rutile, anatase, and brookite but can be applied without particular limitation. The inventors understand that the rutile has relatively high antimicrobial and antiviral performance. The rutile has a large true specific gravity and thus hardly dispersed in liquid in order to make a transparent coating agent. It is important from the practical viewpoint to use anatase or brookite for a coating agent with high transparency even though anatase and brookite have antimicrobial and antiviral performance slightly inferior to rutile. Therefore, the crystal structure of titanium oxide may be selected depending on the productivity and the use.

From the viewpoint of the use in a room, the photocatalytic material is preferably a visible light responsive photocatalyst.

Particularly, the photocatalytic material is preferably a visible light responsive photocatalyst in which the surface of (A) a substrate selected from titanium oxide and tungsten oxide is modified with at least one selected from (B) a copper (II) ion and an iron (III) ion or in which the surface of (C) a substrate selected from the group consisting of titanium oxide doped with a transition metal, titanium oxide doped with a non-metal, tungsten oxide doped with a transition metal, and tungsten oxide doped with a non-metal is modified with at least one selected from (B) a copper (II) ion and an iron (III) ion.

The above-mentioned titanium oxide (A) is not particularly limited. For example, monocrystalline titanium oxides each having the crystal structure of anatase, rutile, or brookite; or titanium oxide with a combination of two or more crystal structures can be used. The above-mentioned tungsten oxide (A) is not particularly limited. For example, tungsten oxides each having a triclinic crystal structure, a monoclinic crystal structure, and a tetragonal crystal structure can be used.

The above-mentioned copper (II) ion and iron (III) ion (B) are not particularly limited as long as these ions can be modified in a photocatalyst to improve the photocatalytic activity under visible light irradiation. For example, the copper (II) ion and iron (III) ion modified in a photocatalyst include oxides, hydroxides, chlorides, nitrates, sulfates, and acetate, or organic complexes of the copper (II) ion and iron (III) ion, respectively. Among these, oxides and hydroxides are preferable.

The above-mentioned transition metal and non-metal (C) are not particularly limited as long as these are doped in titanium oxide to produce an impurity level so that the absorption of visible light can be increased. For example, the transition metal includes vanadium, chromium, iron, copper, ruthenium, rhodium, tungsten, gallium, and indium. The non-metal includes carbon, nitrogen, and sulfur. In a titanium oxide crystal, in order to keep the charge balance, a plurality of transition metals can be doped, or a transition metal and a non-metal can be codoped.

As these catalysts, the exemplary copper (II) ion-modified titanium oxide is described in the paragraphs 0029-0032 in patent document of JP2011-079713A. The exemplary copper (II) ion-modified tungsten oxide is described in the paragraphs 0028-0031 in patent document of JP2009-226299A. The exemplary titanium oxide codoped with copper (II) ion-modified tungsten and gallium is described in the paragraphs 0013-0021 in patent document of JP2011-031139A.

The antimicrobial and antiviral composition of the present invention is produced after the steps of: adding a basic substance and a reducing agent other than a saccharide having an aldehyde group in aqueous solution of a copper (II) compound and then synthesizing cuprous oxide particles; mixing the obtained cuprous oxide particles with aqueous solution of a saccharide having an aldehyde group to adjust the content of a saccharide having an aldehyde group to from 0.5 to 10 mass part based on the obtained cuprous oxide particles of 100 mass part; and separating a solid content from the mixture and then pulverizing the solid content.

Each step will be explained below.

Step of Synthesizing Cuprous Oxide Particles

The copper (II) compound, soluble in water, includes copper (II) sulfate, copper (II) chloride, copper (II) nitrate, copper (II) acetate, and copper (II) hydroxide. Copper (II) sulfate is preferable. The concentration of a copper (II) compound in the aqueous solution to be used for the synthesis is preferably 0.05 to 1 mol/L, more preferably 0.1 to 0.5 mol/L in copper (II) ion equivalent.

The basic substance may be an organic or an inorganic substance, including sodium hydroxide, potassium hydroxide, lithium hydroxide, ammonia, triethylamine, and tetrabutylammonium hydroxide. In particular, sodium hydroxide and tetrabutylammonium hydroxide are preferable. The additive amount of the basic substance is preferably 0.5 to 5 molar times, more preferably 1 to 3 molar times, based on the mole number of the copper (II) ion.

The reducing agent other than a saccharide having an aldehyde group includes aqueous solutions of hydroxylamine sulfate, hydroxylamine nitrate, sodium sulfite, sodium hydrogen sulfite, sodium dithionite, hydrazine sulfate, hydrazine, and sodium phosphite. In particular, aqueous solution of hydrazine is preferable. The additive amount of the reducing agent is preferably 0.1 to 1 molar times, more preferably 0.2 to 0.5 molar times based on the mole number of the copper (II) ion.

In the synthesis condition, the temperature is preferably 10 to 90° C., more preferably 30 to 60° C.

Step of Mixing

The saccharide having an aldehyde group includes the above-mentioned saccharides. The concentration of reducing sugar in aqueous solution is preferably 0.1 to 2 mol/L, more preferably 0.5 to 1.5 mol/L.

In the finally obtained antimicrobial and antiviral composition, the mixed amount of aqueous solution of reducing sugar is set to adjust the content of a saccharide having an aldehyde group to from 0.5 to 10 mass part based on the obtained cuprous oxide particles of 100 mass part.

Step of Pulverizing

After mixing with the aqueous solution of reducing sugar, the solid content is dried, separated, and then pulverized to obtain the antimicrobial and antiviral composition of the present invention.

When a photocatalytic material is contained, it is only necessary to mix a solid content or a dispersion of the cuprous oxide particles and reducing sugar after the step of mixing, with a dispersion of a photocatalytic material.

Filtration with a membrane filter can be adopted to separate the solid content. After separated, the solid content is dried at 50 to 80° C. as required, and then pulverized in a usual way. At this time, in order to adjust the specific surface area of the cuprous oxide particles within the range of 5 to 100 m$^2$/g, the pulverization is conducted with a pulverization device with weak energy. For example, the pulverization device includes a ball mill, a mixer, a pot mill, and an agate mortar.

2. Dispersion of Antimicrobial and Antiviral Composition

The dispersion of the antimicrobial and antiviral composition of the present invention is preferable any one of the following two aspects.

The first dispersion of the antimicrobial and antiviral composition of the present invention contains the above-mentioned antimicrobial and antiviral composition of the present invention of 1 to 30% by mass, a non-aqueous organic solvent of 60 to 98.99% by mass, and a basic substance being soluble in the non-aqueous organic solvent of 0.01 to 10% by mass.

The second dispersion of the antimicrobial and antiviral composition of the present invention contains the above-mentioned antimicrobial and antiviral composition of the present invention of 1 to 30% by mass, a non-aqueous organic solvent of 40 to 98.98% by mass, a basic substance being soluble in the non-aqueous organic solvent of 0.01 to 10% by mass, and a surfactant being soluble in the non-aqueous organic solvent of 0.01 to 20% by mass.

The first and the second dispersions of the antimicrobial and antiviral composition of the present invention are referred to collectively as the dispersion of the present invention.

In the dispersion of the present invention, the content ratio is adjusted as described above, so that the antimicrobial and antiviral composition can be dispersed uniformly and preserved stably.

The antimicrobial and antiviral composition is contained in 1% by mass or more, so that the antimicrobial and antiviral performance can be exerted. The antimicrobial and antiviral composition is contained in 30% by mass or less, so that the dispersion of the present invention can be preserved stably to improve the convenience. The concentration of the antimicrobial and antiviral composition in the dispersion is preferably 2 to 20% by mass, more preferably 3 to 10% by mass.

The concentration of the basic substance of 0.01% by mass or more allows the dispersion of the present invention to be basic, so that the cuprous oxide particles can be prevented from being dissolved. Furthermore, the basic substance with a concentration of 10% by mass or less reduces a residue of a basic substance of a film formed from the dispersion of the present invention, so that the antimicrobial and antiviral performance of cuprous oxide particles can be maintained. The concentration of a basic substance in the dispersion of the antimicrobial and antiviral composition is preferably 0.05 to 7% by mass, more preferably 0.08 to 5% by mass.

The non-aqueous organic solvent is an organic solvent other than water, including ethanol, methanol, 2-propanol, denatured alcohol, methyl ethyl ketone (MEK), and n-propyl acetate (NPAC).

The reason for using a non-aqueous organic solvent is because cuprous oxide is easily oxidized into divalent copper in water but hardly oxidized in non-aqueous solvent.

The basic substance soluble in non-aqueous organic solvent may be an organic or an inorganic substance, including sodium hydroxide, potassium hydroxide, lithium hydroxide, ammonia, triethylamine, and tetrabutylammonium hydroxide. In particular, sodium hydroxide and tetrabutylammonium hydroxide are preferable. The solubility of the basic substance is preferably 0.05 g or more based on the non-aqueous organic solvent of 100 g.

The second dispersion of the antimicrobial and antiviral composition of the present invention contains a surfactant soluble in a non-aqueous organic solvent. Accordingly, containing the surfactant reduces the interparticle agglomeration of the antimicrobial and antiviral composition, and provides steric hindrance, so that the dispersion can be stabilized. The surfactant with a content of less than 0.01% by mass lowers the dispersibility of the dispersion to precipitate the antimicrobial and antiviral composition. The surfactant with a content of more than 20% by mass increases amount of the remained surfactant in a film formed from the dispersion, so that the antimicrobial and antiviral performance of the film is lowered. The content of the surfactant is preferably 0.05 to 15% by mass, more preferably 0.08 to 10% by mass.

The surfactant soluble in a non-aqueous organic solvent is preferably anon-ionic surfactant, for example, including glycerine fatty acid ester, sorbitan fatty acid ester, and saccharose fatty acid ester as the ester type, and fatty alcohol ethoxylate, polyoxyethylene alkylphenyl ether, octylphenoxy polyethoxyethanol (Triton™ X-100), and alkyl glycoside as the ether type. In particular, octylphenoxy polyethoxyethanol is preferable.

3. Coating Agent Containing Antimicrobial and Antiviral Composition, Antimicrobial and Antiviral Film, and Antimicrobial and Antiviral Article The coating agent containing the antimicrobial and antiviral composition of the present invention contains the dispersion of the antimicrobial and antiviral composition of the present invention, and a binder component being curable under an environment of 10 to 120° C. The binder component may be an inorganic binder or an organic binder. Given the degradation of a binder by a photocatalytic material, an inorganic binder is preferable. The type of the binder is not particularly limited, for example, including a silica binder, a zirconia binder, an alumina binder, and a titania binder, and a combination thereof. In particular, a silica binder or a zirconia binder is preferable.

The content of the binder is preferably 0.5 to 10% by mass, more preferably 1 to 8% by mass. The binder with a content of 0.5 to 10% by mass can disperse a coating agent stably and can allows a cured film to uniformly adhere to a substrate.

The antimicrobial and antiviral film of the present invention is formed by appling and then curing the coating agent containing the antimicrobial and antiviral composition of the present invention. The substrate, on which the coating agent containing the antimicrobial and antiviral composition of the present invention is applied, includes metal, ceramics, glass, fiber, nonwoven fabric, film, plastic, rubber, paper, and wood, the surface of which paint or the like may be applied. The method of applying is not limited so that a spin coating method, a dip coating method, a spray coating method, or the like can be adopted.

The curing temperature after applying the coating agent depends on a binder component to be used but is preferably about 20 to 80° C. The thickness of the antimicrobial and antiviral film of the present invention obtained by curing is preferably 0.05 to 1 µm, more preferably 0.1 to 0.5 µm.

The antimicrobial and antiviral article of the present invention has the antimicrobial and antiviral film of the present invention on at least one part (for example, to be touched by people) of the surface, for example, including articles such as construction materials, sanitary materials, and antifouling materials.

EXAMPLES

The present invention will be explained specifically in reference to Examples below.

The crystal peak attribution of cuprous oxide particles of the antimicrobial and antiviral composition obtained in each Example was determined by XRD measurement. In the XRD measurement, a copper target was used, a Cu-Kα1 line was used, the tube voltage was 45 kV, the tube current was 40 mA, the measurement range was 2θ=20-80 deg., the sampling width was 0.0167 deg, and the scan rate was 1.1 deg/min. X'PertPRO available from PANalytical B.V. was used for this measurement.

The BET specific surface area of cuprous oxide particles of the antimicrobial and antiviral composition obtained in each Example was measured by using the automatic surface area analyzer "Macsorb®, HM model-1208" available from Mountech Co., Ltd.

Example 1

1000 mL of distilled water was heated to 50° C., and then 52.25 g of copper (II) sulfate pentahydrate was added while being stirred to be dissolved completely. Then, 200 mL of 2 mol/L aqueous sodium hydroxide solution and 28 mL of 2 mol/L aqueous hydrazine hydrate solution were simultaneously added. After the mixture was vigorously stirred for 1 minute, the dispersion in which cuprous oxide particles were dispersed was obtained. Then, 300 mL of 1.2 mol/L aqueous glucose solution was added and stirred for 1 minute. The mixture was filtered with a membrane filter of 0.3 µm, and then the filtered substance was washed with 1000 mL of distilled water to collect the solid content. After dried at 60° C. for 3 hours, the solid content was pulverized with an agate mortar to obtain the antimicrobial and antiviral composition with 1.5 mass part of glucose coexisting based on the cuprous oxide particles of 100 mass part. FIG. 1 shows a SEM image of the antimicrobial and antiviral composition.

The BET specific surface area of the cuprous oxide particles obtained by filtering the dispersion in which cuprous oxide particles were dispersed was 29 m$^2$/g according to the nitrogen adsorption method.

Comparative Example 1

The dispersion in which cuprous oxide particles were dispersed was generated in the same way as that of Example 1. Then, without adding the aqueous glucose solution, the mixture was filtered with a membrane filter of 0.3 µm, the filtered substance was washed with the distilled water to collect the solid content. After dried at 60° C. for 3 hours, and then the solid content was pulverized with an agate mortar to obtain cuprous oxide particles. The BET specific surface area of the obtained cuprous oxide particles was 29 m²/g according to the nitrogen adsorption method.

The quantitative determination of glucose in the antimicrobial and antiviral composition obtained in Example 1 was carried out as follows. Specifically, the carbon content was measured by using a high-frequency heating-infrared absorption method, and then the amount of coexisting glucose was calculated from the carbon content. The carbon content contained in Comparative Example 1 was defined as the carbon content mixed in experimental operation. By subtracting this carbon content from the remaining carbon content, the amount of the glucose contained in cuprous oxide particles was calculated. The result is shown in Table 1. The glucose in other Examples was calculated in this way.

TABLE 1

|  | Carbon content (% by mass) | Carbon content excluding carbon content of Comparative Example 1 (% by mass) | Glucose equivalent (mass part) |
| --- | --- | --- | --- |
| Example 1 | 0.78 | 0.58 | 1.5 |
| Comparative Example 1 | 0.20 | 0 | 0 |

Figure 2A:
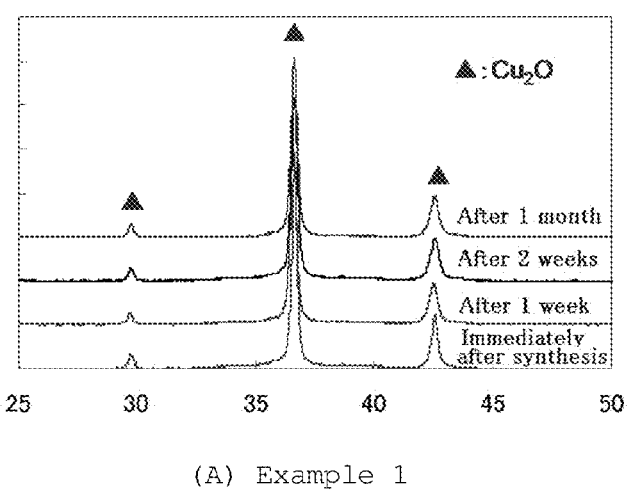
FIG. 2A shows the change in the X-ray diffraction pattern of the antimicrobial and antiviral composition obtained in Example 1.
Figure 2B:
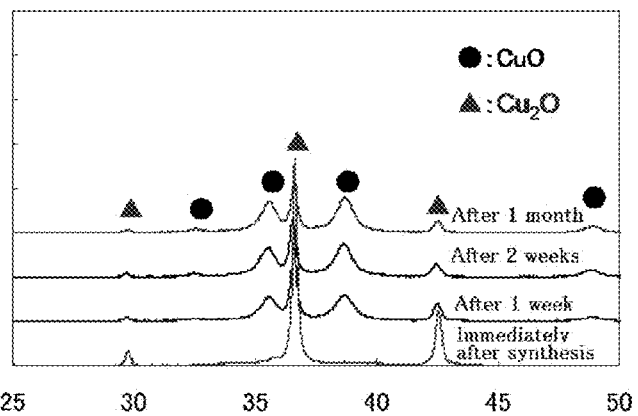
FIG. 2B shows the change in the X-ray diffraction pattern of the cuprous oxide obtained in Comparative Example 1.

The antimicrobial and antiviral composition obtained in Example 1 and the cuprous oxide particles obtained in Comparative Example 1 were exposed in the air and observed by the XRD measurement after 1 week, 2 weeks, and 1 month. The result is shown in FIGS. 2A and 2B. In Example 1, the change of the peak intensity of cuprous oxide ($Cu_2O$) can hardly be seen (FIG. 2A). In Comparative Example 1, the peak of copper oxide (CuO) appeared from the oxidization of cuprous oxide (FIG. 2B). According to this experimentation, it was confirmed that the coexistence of very small amount of glucose inhibited the oxidation of cuprous oxide.

Example 2

1000 mL of distilled water was heated to 50° C., and then 52.25 g of copper (II) sulfate pentahydrate was added while being stirred to be dissolved completely. Then, 200 mL of 2 mol/L aqueous sodium hydroxide solution and 28 mL of 2 mol/L aqueous hydrazine hydrate solution were simultaneously added. After the mixture was vigorously stirred for 1 minute, the stirred mixture was filtered with a membrane filter of 0.3 μm, and then the filtered substance was washed with 1000 mL of distilled water to collect the solid content. After dried at 60° C. for 3 hours, and then the solid content was pulverized with an agate mortar to obtain cuprous oxide particles. 1 g of the obtained cuprous oxide particles was suspended in 50 mL of ethanol solution, aqueous glucose solution equivalent to 5 mass part of glucose based on the cuprous oxide particles of 100 mass part was added, and then the solvent was evaporated to obtain cuprous oxide particles with 5 mass part of glucose coexisting (the antimicrobial and antiviral composition).

The BET specific surface area of the cuprous oxide particles obtained in Example 2 was 28 m²/g according to the nitrogen adsorption method.

Example 3

Except that aqueous glucose solution equivalent to 10 mass part of the glucose content based on the cuprous oxide particles of 100 mass part was added, cuprous oxide particles with 10 mass part of glucose coexisting (the antimicrobial and antiviral composition) obtained in the same way as that of Example 2.

The BET specific surface area of the cuprous oxide particles obtained in Example 3 was 28 m²/g according to the nitrogen adsorption method.

Example 4

Anatase titanium oxide (the trade name "FP-6" available from Showa Titanium Co., Ltd.) was suspended in 2-propyl alcohol (hereafter referred to as "IPA") to prepare a dispersion with a solid content concentration of 5% by mass. After 2 mass part of Triton™ X-100 (octylphenoxy polyethoxyethanol available from KANTO CHEMICAL CO., INC.) equivalent to the titanium oxide of 100 mass part was added, 2 mass part of tetrabutylammonium hydroxide equivalent to the titanium oxide (40 mass % aqueous tetrabutylammonium hydroxide solution (available KANTO CHEMICAL CO., INC.)) was added.

Then, the suspension was dispersed with a bead mill by using 0.1 mm-sized medium to obtain a dispersion (hereafter referred to as "FP-6 IPA dispersion"). "The cuprous oxide particles with 1.5 mass part of glucose coexisting" obtained in Example 1 were dispersed in the FP-6 IPA dispersion to obtain the dispersion of the antimicrobial and antiviral composition so as to adjust the content of the cuprous oxide particles to 3 mass part based on the titanium oxide of 100 mass part.

The obtained dispersion of the antimicrobial and antiviral composition was applied to a glass plate (50 mm×50 mm×1 mm) so as to adjust the solid content to 1.5 mg/25 cm². The solvent on the glass plate was evaporated, and then the viral inactivation capacity was evaluated (the evaluation method is described later). The result is shown in FIG. 3.

Figure 3:
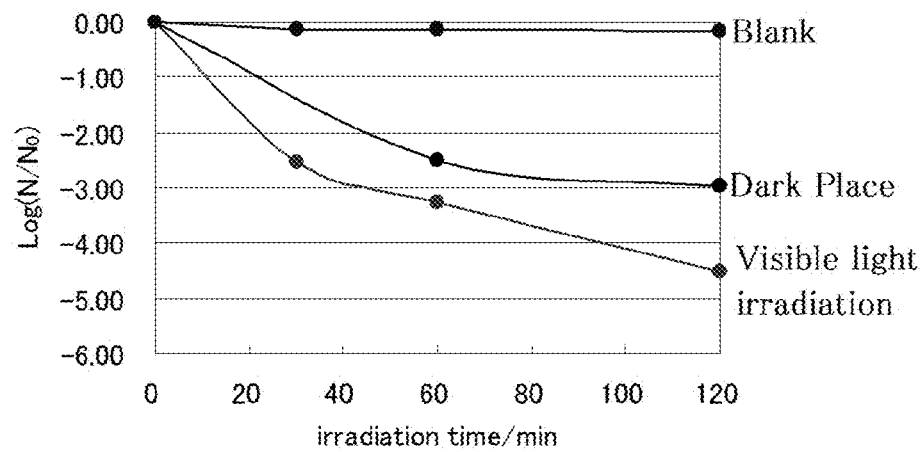
FIG. 3 shows the antiviral property of Example 4.

"Blank" seen in FIG. 3 shows the evaluation result of the viral inactivation capacity of only a glass plate.

"Dark place" shows the evaluation result of under dark conditions of a glass plate on which the dispersion was applied.

"Visible light irradiation" shows the evaluation result of under visible light irradiation of a glass plate on which the dispersion was applied.

The visible light irradiation was conducted in conditions in which light was irradiated from a white fluorescent lamp through an N-113 optical filter, in which a light of 400 nm or less was cut. The light intensity was 800 Lux.

As shown in FIG. 3, the viral inactivation capacity of only a glass plate was not demonstrated. The viral inactivation capacity of the glass plate on which the dispersion was applied was demonstrated even in a dark place. The glass plate on which the dispersion was applied demonstrated higher viral inactivation capacity in visible light irradiation. Therefore, it can be seen that the antimicrobial and antiviral composition of the present invention demonstrated excellent viral inactivation capacity. Furthermore, it was confirmed that the antimicrobial and antiviral composition of the present invention used with a photocatalytic material (FP-6 titanium oxide) had an effect on the improvement of viral inactivation capacity by light irradiation in a dark place.

Example 5

50 g of brookite titanium oxide (NTB-01 available from Showa Titanium Co., Ltd.) was suspended in 1000 mL of distilled water, $CuCl_2.2H_2O$ 0.133 g (available from KANTO CHEMICAL CO., INC.) was added so as to support 0.1 mass part of support copper (II) ion based on the titanium oxide of 100 mass part, and then the mixture was heated at 90° C. while being stirred for 1 hour. The heated mixture was washed and then dried to obtain copper (II) ion-modified titanium oxide. Except that the copper (II) ion-modified titanium oxide was used instead of FP-6, a dispersion of the antimicrobial and antiviral composition was obtained in the same way as that of Example 4.

Example 6

50 g of tungsten oxide (available from Wako Pure Chemical Industries, Ltd.) was suspended in 1000 mL of distilled water, $CuCl_2.2H_2O$ 0.133 g (available from KANTO CHEMICAL CO., INC.) was added so as to support 0.1 mass part of support copper (II) ion based on the tungsten oxide of 100 mass part, and then the mixture was heated at 90° C. while being stirred for 1 hour. The heated mixture was washed and then dried to prepare copper (II) ion-modified tungsten oxide. Except that the copper (II) ion-modified tungsten oxide was used instead of FP-6, a dispersion of the antimicrobial and antiviral composition was obtained in the same way as that of Example 4.

Example 7

10 g of titanium oxide (with the crystal structure of rutile, available from TAYCA CORPORATION) was suspended in 20 mL of ethanol (available from Wako Pure Chemical Industries, Ltd.) to prepare a titanium oxide suspension. 1 g of tungsten hexachloride (available from Sigma-Aldrich Co. LLC) was dissolved in 10 mL of ethanol to prepare a tungsten solution. 1 g of gallium (III) nitrate monohydrate (available from Sigma-Aldrich Co. LLC) was dissolved in 10 mL of ethanol to prepare a gallium solution. The tungsten solution and the gallium solution were mixed with the titanium oxide suspension so as to adjust the molar ratio of tungsten:gallium:titanium to 0.03:0.06:0.91. While the mixture was stirred, the ethanol solvent was evaporated. The obtained powder was heated at 950° C. for 3 hours. As a result, the titanium oxide codoped with tungsten and gallium was obtained. 5 g of the titanium oxide codoped with tungsten and gallium was suspended in 100 g of distilled water, 0.013 g of $CuCl_2.2H_2O$ (available from KANTO CHEMICAL CO., INC.) was added so as to support 0.1 mass part of support copper (II) ion based on 100 mass part of the titanium oxide codoped with tungsten and gallium, and then the mixture was heated at 90° C. while being stirred for 1 hour. The heated mixture was washed and then dried to prepare copper (II) ion-modified titanium oxide codoped with tungsten and gallium. Except that the copper (II) ion-modified titanium oxide codoped with tungsten and gallium was used instead of FP-6, a dispersion of the antimicrobial and antiviral composition was obtained in the same way as that of Example 4.

Comparative Example 2

1 g of the cuprous oxide particles obtained in Comparative Example 1 were suspended in 50 mL of ethanol solution, aqueous glucose solution equivalent to 0.3 mass part of glucose based on the cuprous oxide particles of 100 mass part was added, and then the solvent was evaporated to obtain cuprous oxide particles with 0.3 mass part of glucose coexisting.

Comparative Example 3

1 g of the cuprous oxide particles obtained in Comparative Example 1 were suspended in 50 mL of ethanol solution, aqueous glucose solution equivalent to 12 mass part of glucose based on the cuprous oxide particles of 100 mass part was added, and then the solvent was evaporated to obtain cuprous oxide particles with 12 mass part of glucose coexisting.

Comparative Example 4

1 g of commercially available cuprous oxide particles (the BET specific surface area: 1 $m^2$/g, the trade name: "Regular", available from FURUKAWA CHEMICALS CO., LTD.) were suspended in 50 mL ethanol solution, aqueous glucose solution equivalent to 1.5 mass part of glucose based on the cuprous oxide particles of 100 mass part was added, and then the solvent was evaporated to obtain cuprous oxide particles with 1.5 mass part of glucose coexisting. 1 g of the obtained cuprous oxide particles were dispersed in 100 ml of ethanol to obtain a dispersion. The dispersion was applied to a glass plate to form a film coated with cuprous oxide so as to adjust the application amount to 8 mg/$m^2$.

Comparative Example 5

Except that the coating amount was adjusted to 24 mg/$m^2$, a film coated with cuprous oxide was formed in the same way as that of Comparative Example 4.

Comparative Example 6

The cuprous oxide particles obtained in Comparative Example 1 was left in the air for 30 days to be oxidized into copper (II) oxide ones and then mixed with an FP-6 IPA dispersion in the same way as that of Example 4 to obtain a copper (II) oxide/titanium oxide dispersion.

Comparative Example 7

The cuprous oxide particles obtained in Comparative Example 1 was mixed with an FP-6 IPA dispersion in the same way as that of Example 4 to obtain a cuprous (I) oxide/titanium oxide dispersion.

Comparative Example 8

The cuprous oxide particles obtained in Comparative Example 1 was mixed with an IPA dispersion of copper (II) ion-modified titanium oxide in the same way as that of Example 5 to obtain a cuprous (I) oxide/copper (II) ion-modified titanium oxide dispersion.

Evaluation of Viral Inactivation Capacity: Measurement of $LOG(N/N_0)$

The viral inactivation capacity was evaluated by the following method in a model experiment using bacteriophages. The method using the inactivation capacity for bacteriophages as a model of viral inactivation capacity is described in Appl. Microbiol Biotechnol., 79, pp.127-133, 2008, for example, and known for obtaining a reliable result.

A filter paper was placed in a deep culture plate, and then a small amount of sterilized water was added. A grass platform with a thickness of about 5 mm was placed on the filter paper. On the grass platform, glass plates (50 mm×50 mm×1 mm) were placed. On these glass plates, the antimicrobial and antiviral compositions of Examples 1-3 and the samples of Comparative Examples 1-3 were applied to adjust the solid content to 0.02 mg/25 $cm^2$, respectively, and the dispersions of the antimicrobial and antiviral compositions of Examples 4-7 and the samples of Comparative Examples 6-8 were applied to adjust the solid content to 1.5 mg/25 cm², respectively. A predetermined concentration of suspension 100 μL of previously naturalized QB phages (NBRC20012) was added dropwise to each glass plate, and then a PET (polyethylene terephthalate) OHP film was placed over each glass plate in order to contact the sample surface with the phages. The deep culture plate was covered with a lid to prepare a measurement set. A plurality of the same measurement sets was prepared.

As a light source, a 15 W white fluorescent lamp (full white fluorescent lamp, FL15N available from Panasonic Corporation) mounted with a UV cut filter (KU-1000100 available from KING WORKS Co., Ltd.) was used. Then, the plurality of measurement sets were left at the position at which the illuminance was 800 Lux (measured with an illuminance meter, IM-5 available from TOPCON CORPORATION). After a predetermined time, the phage concentration of the sample on each glass plate was determined.

The phage concentration was measured by the following method. The sample on each glass plate was immersed in a collecting liquid (SM buffer) 10 mL and then was shaken with a shaker for 10 minutes. This phage collecting liquid was diluted appropriately, the diluted liquid was mixed with a culture solution ($OD_{600}$>1.0, $1\times10^8$ CFU/mL) of separately cultured *E. coli* (NBRC13965), and then the mixture was left in a constant temperature room of 37° C. to infect the phages with the *E. coli*. This liquid was poured to an agar medium, the liquid-poured medium was cultured at 37° C. for 15 hours, and then the number of phage plaques was visually measured. The obtained number of plaques was multiplied by the dilution ratio of the phage collecting liquid to determine the phage concentration N.

Based on the initial phage concentration $N_o$ and the phage concentration N after a predetermined time, the phage relative concentration ($LOG(N/N_0)$) was determined. Each coated film of Comparative Examples 4 and 5 was left on a glass platform with a thickness of 5 mm as it is, and then the phage concentration was determined.

The result of viral inactivation capacity evaluated under various conditions is shown in Tables 2-4.

TABLE 2

| | Glucose content (mass part) | Evaluation immediately after synthesis $LOG(N/N_0)$ (1 h irradiation) | Evaluation 1 month after synthesis $LOG(N/N_0)$ (1 h irradiation) |
|---|---|---|---|
| Example 1 | 1.5 | −5.0 | −5.1 |
| Example 2 | 5 | −4.1 | −4.1 |
| Example 3 | 10 | −3.5 | −3.4 |
| Comparative Example 1 | 0 | −4.8 | −0.9 |
| Comparative Example 2 | 0.3 | −4.9 | −0.8 |
| Comparative Example 3 | 12 | −2.0 | −2.0 |

Table 2 shows the viral inactivation capacity of the cuprous oxide particles immediately (within 5 days) after the synthesis and after 1 month (30 days or more) according to the various amounts of glucose. The amount of the coated film was 8 mg/m².

In Examples 1-3, the viral inactivation capacity was decreased as the amount of glucose increased. In any of these Examples, the evaluation results after the synthesis and after 1 month show no changes in the viral inactivation capacity. Comparative Example 3 had an antioxidant effect but an overall low viral inactivation capacity due to the existence of a large amount of glucose.

In Comparative Examples 1 and 2, each viral inactivation capacity after the synthesis was high while each viral inactivation capacity after 1 month was significantly decreased. This may occur due to a small amount of glucose and ineffective antioxidation.

TABLE 3

| | Specific surface area (m²/g) | Coating amount (mg/m²) | $LOG(N/N_0)$ (1 h irradiation) |
|---|---|---|---|
| Example 1 | 29 | 8 | −5.0 |
| Comparative Example 4 | 1 | 8 | −1.0 |
| Comparative Example 5 | 1 | 24 | −1.9 |

Table 3 shows the comparison of the viral inactivation capacity of Example 1 with those of Comparative Examples 4 and 5.

Since the cuprous oxide particles synthesized in Example 1 had a large BET specific surface area, the cuprous oxide particles obviously demonstrate higher activity than a commercially available cuprous oxide with a small BET specific surface area, in which glucose was added. Therefore, high viral inactivation capacity can be expected by using the antimicrobial and antiviral composition of the present invention even with a small coating amount.

TABLE 4

| | Evaluation immediately after synthesis LOG(N/N0) | | Evaluation 1 month after synthesis LOG(N/N0) | |
|---|---|---|---|---|
| | Dark place | 2 h visible light irradiation | Dark place | 2 h visible light irradiation |
| Example 4 | −3.1 | −4.5 | −3.0 | −4.5 |
| Example 5 | −3.1 | −5.2 | −3.1 | −5.2 |
| Example 6 | −3.2 | −6.1 | −3.0 | −6.0 |
| Example 7 | −3.2 | −5.4 | −2.9 | −5.5 |
| Comparative Example 6 | −1.5 | −2.5 | −1.1 | −2.3 |
| Comparative Example 7 | −3.2 | −4.7 | −2.2 | −3.1 |
| Comparative Example 8 | −3.2 | −5.2 | −2.1 | −3.5 |

Table 4 shows the antiviral performance immediately after the material combined with a photocatalytic material was synthesized and after the material was left in the air for 1 month (30 days or more).

Examples 4-7 are the antimicrobial and antiviral compositions combined with glucose, cuprous oxide, and a photocatalyst. Comparative Examples 6-8 are the antimicrobial and antiviral compositions combined with cuprous oxide and a photocatalyst but not glucose.

In comparison of the evaluation immediately after synthesis and that after 1 month, it can be seen that Examples 4-7 in which glucose exists can maintain superior viral inactivation capacity in a dark place or in visible light irradiation. On the other hand, the viral inactivation capacity was decreased in Comparative Examples 6-8 without glucose.

Examples 4-7 and Comparative Examples 6-8 in visible light irradiation demonstrate superior viral inactivation capacity than those in the dark place because of the combination with a photocatalyst. It may be because copper (I) was increased by the oxidation-reduction of the photocatalyst under visible light irradiation to contribute to the antiviral performance. However, even if combined with a photocatalyst, Comparative Examples 6-8 had lower viral inactivation capacity than Examples 4-7.

It can be confirmed from the above that the antimicrobial and antiviral composition combined with glucose, cuprous oxide, and a photocatalyst like any of Examples 4-7 can maintain high viral inactivation capacity even after time passes.

The invention claimed is:

1. An antimicrobial and antiviral composition comprising cuprous oxide particles having a BET specific surface area of 5 to 100 $m^2/g$; and a saccharide having an aldehyde group, wherein the content of the saccharide having an aldehyde group is 0.5 to 10 mass part based on the cuprous oxide particles of 100 mass part.

2. The antimicrobial and antiviral composition according to claim 1, further comprising a photocatalytic material, wherein the content of the photocatalytic material is 70 to 99.9% by mass based on the total amount of the cuprous oxide particles, the saccharide having an aldehyde group, and the photocatalytic material.

3. The antimicrobial and antiviral composition according to claim 2, wherein the photocatalytic material comprises at least one selected from titanium oxide and tungsten oxide.

4. The antimicrobial and antiviral composition according to claim 2, wherein the photocatalytic material is a visible light responsive photocatalyst in which a substrate selected from (A) titanium oxide and tungsten oxide is modified with at least one selected from (B) a copper (II) ion and an iron (III) ion.

5. The antimicrobial and antiviral composition according to claim 2, wherein the photocatalytic material is a visible light responsive photocatalyst in which a substrate selected from the group consisting of (C) titanium oxide doped with a transition metal; titanium oxide doped with at least one non-metal of carbon, nitrogen, and sulfur; tungsten oxide doped with a transition metal; and tungsten oxide doped with at least one non-metal of carbon, nitrogen, and sulfur is modified with at least one selected from (B) a copper (II) ion and an iron (III) ion.

6. A dispersion of an antimicrobial and antiviral composition, comprising 1 to 30% by mass of the antimicrobial and antiviral composition according to claim 1; 60 to 98.99% by mass of a non-aqueous organic solvent; and 0.01 to 10% by mass of a basic substance being soluble in the non-aqueous organic solvent.

7. A dispersion of an antimicrobial and antiviral composition, comprising 1 to 30% by mass of the antimicrobial and antiviral composition according to claim 1, 40 to 98.99% by mass of a non-aqueous organic solvent, 0.01 to 10% by mass of a basic substance being soluble in the non-aqueous organic solvent, and 0.01 to 20% by mass of a surfactant being soluble in the non-aqueous organic solvent.

8. A coating agent containing an antimicrobial and antiviral composition, comprising the dispersion of an antimicrobial and antiviral composition according to claim 6, and a binder component being curable under an environment of 10-120° C.

9. An antimicrobial and antiviral film to which the coating agent containing an antimicrobial and antiviral composition according to claim 8 is applied and then cured.

10. An antimicrobial and antiviral article comprising the antimicrobial and antiviral film according to claim 9 on at least one part of the surface.

11. A method of producing an antimicrobial and antiviral composition, comprising the steps of: adding a basic substance and a reducing agent other than a saccharide having an aldehyde group in aqueous solution of a copper (II) compound and then synthesizing cuprous oxide particles; mixing the obtained cuprous oxide particles with aqueous solution of a saccharide having an aldehyde group to adjust the content of a saccharide having an aldehyde group to from 0.5 to 10 mass part based on the obtained cuprous oxide particles of 100 mass part; and separating a solid content from the mixture and then pulverizing the solid content.

* * * * *